United States Patent
Myntti

(10) Patent No.: US 10,045,527 B2
(45) Date of Patent: Aug. 14, 2018

(54) ANTIMICROBIAL SOLID AND METHOD OF MAKING SAME

(71) Applicant: NEXT SCIENCE IP HOLDINGS PTY LTD, Chatswood, NSW OT (AU)

(72) Inventor: Matthew Franco Myntti, St. Augustine, FL (US)

(73) Assignee: Next Science IP Holdings Pty Ltd, Chatswood, New South Wales (AU)

( * ) Notice: Subject to any disclaimer, the term of this patent is extended or adjusted under 35 U.S.C. 154(b) by 0 days.

(21) Appl. No.: 14/485,748

(22) Filed: Sep. 14, 2014

(65) Prior Publication Data

US 2015/0004203 A1    Jan. 1, 2015

Related U.S. Application Data

(63) Continuation of application No. 13/468,767, filed on May 10, 2012.

(60) Provisional application No. 61/484,558, filed on May 10, 2011.

(51) Int. Cl.
| | | |
|---|---|---|
| *A01N 25/10* | (2006.01) | |
| *A01N 25/30* | (2006.01) | |
| *A01N 25/08* | (2006.01) | |

(52) U.S. Cl.
CPC ............. *A01N 25/10* (2013.01); *A01N 25/08* (2013.01)

(58) Field of Classification Search
CPC ......... A01N 25/10; A01N 25/08; A01N 25/30
See application file for complete search history.

(56) References Cited

U.S. PATENT DOCUMENTS

| | | |
|---|---|---|
| 5,348,678 A | 9/1994 | Hodam, Jr. et al. |
| 6,673,053 B2 | 1/2004 | Wang et al. |
| 8,784,790 B2 | 7/2014 | Myntti et al. |
| 8,940,792 B2 | 1/2015 | Myntti |
| 9,220,725 B2 | 12/2015 | Krishnan |
| 9,314,017 B2 | 4/2016 | Myntti |
| 2003/0147826 A1 | 8/2003 | Anthony et al. |
| 2007/0166344 A1* | 7/2007 | Qu .......................... A61L 15/46 424/423 |
| 2008/0317702 A1 | 12/2008 | Edgington et al. |
| 2010/0086576 A1* | 4/2010 | Myntti ................... A01N 25/30 424/405 |
| 2010/0260691 A1 | 10/2010 | Narayanan et al. |
| 2012/0288469 A1 | 11/2012 | Myntti |
| 2014/0242188 A1 | 8/2014 | Myntti |
| 2016/0073628 A1 | 3/2016 | Myntti |

FOREIGN PATENT DOCUMENTS

WO    WO 2009103717 A1 *    8/2009

OTHER PUBLICATIONS

Rivero et al.; title: An antibacterial coating based on a polymer/sol-gel hybrid matrix loaded with silver nanoparticles; Nanoscale Res Lett.; vol. 6(1):305; pp. 1-7; published Apr. 7, 2011.*
Author: Cheng-Kuang Chan; Title: Effect of hydrogen bonding on the glass transition behavior of poly(acrylic acid)/silica hybrid materials prepared by sol-gel process; Polymer; vol. 42, Issue 14, Jun. 2001, pp. 6089-6093.*
Notice of Allowance and Fees Due for U.S. Appl. No. 15/075,147, dated May 23, 2016—7 pp.
Patent examination report in AU appl. No. 2015261645, dated Nov. 23, 2016.
Second examination report in AU appl. No. 2015261645, dated Apr. 10, 2017.
S.Z. Siddiqui et al., "Next-Science: A Novel Antimicrobial Agent that Inhibits Biofilm Development by *Esceherichia coli* Clinical Isolates on Urinary Tract Catheters," J. Med. Microb. Diagn., 2017, vol. 6, issue 4, Dec. 21, 2017 (open-access via CCA license).

* cited by examiner

*Primary Examiner* — Yanzhi Zhang
(74) *Attorney, Agent, or Firm* — Zollinger & Burleson Ltd.

(57) ABSTRACT

A solid material adapted to kill bacteria in planktonic, spore and biofilm states is lethal toward a wide spectrum of gram positive and gram negative bacteria as well as other microbes. The solid material includes a significant amount of one or more surfactants entrained in a crosslinked polymeric network.

10 Claims, No Drawings

ANTIMICROBIAL SOLID AND METHOD OF MAKING SAME

CROSS-REFERENCE TO RELATED APPLICATION

This application is a continuation of U.S. application Ser. No. 13/468,767, filed 10 May 2012 and presently pending, which claims the benefit of U.S. provisional appl. No. 61/484,558 filed 10 May 2011, the entire disclosures of each being incorporated herein by reference.

BACKGROUND INFORMATION

Bacteria is found virtually everywhere and is responsible for a significant amount of disease and infection. Killing and/or eliminating these microorganisms is desirable to reduce exposure and risk of disease.

Bacteria in many environments are present in high concentrations and have developed self preservation mechanisms and, therefore, are extremely difficult to remove and/or eradicate. They can exist in planktonic, spore and biofilm forms.

In a biofilm, bacteria interact with surfaces and form surface colonies which adhere to a surface and continue to grow. The bacteria produce exopolysaccharide (EPS) and/or extracellularpolysaccharide (ECPS) macromolecules that keep them attached to the surface and form a protective barrier effective against many forms of attack. Protection most likely can be attributed to the small diameter of the flow channels in the matrix, which restricts the size of molecules that can transport to the underlying bacteria, and consumption of biocides through interactions with portions of the EPS/ECPS macromolecular matrix.

Bacteria often form spores, which provide additional resistance to eradication efforts. In this form, the bacteria create a hard, non-permeable protein/polysaccharide shell around themselves which prevents attack by materials that are harmful to the bacteria.

Additionally, bacteria in biofilm- or spore forms are down-regulated (sessile) and not actively dividing. This makes them resistant to attack by a large group of antibiotics and antimicrobials, which attack the bacteria during the active parts of their lifecycle, e.g., cell division.

Due to the protection afforded by a macromolecular matrix (biofilm) or shell (spore) and their down-regulated state, bacteria in biofilm- and spore states are very difficult to treat. The types of biocides and antimicrobials effective in treating bacteria in this form are strongly acidic, oxidizing, and toxic, often involving halogen atoms, oxygen atoms, or both. Common examples include concentrated bleach, phenolics, strong mineral acids (e.g., HCl), hydrogen peroxide and the like. Commonly, large dosages of such chemicals are allowed to contact the biofilm or spore for extended amounts of time (up to 24 hours in some circumstances), which makes them impractical for many applications.

Recently developed formulations intended for use in connection with compromised animal/human tissue can solvate a biofilm matrix so that still-living bacteria can be rinsed or otherwise removed from infected tissue; the concentrations of active ingredients in these formulations are too low to effectively kill the bacteria, thus making them ill suited for use as disinfecting agents. More recently, solutions that can disrupt the macromolecular matrix, or bypass and/or disable the defenses inherent in these matrices, allowing lethal doses of antimicrobial ingredients in the solutions to access and kill the bacteria in their biofilm and sessile states have been described; unlike the aforementioned formulations, these solutions can be used as disinfectants.

Most water filtration is accomplished using filters made of materials such as paper, fiber, and synthetic fibers. Unclean, bacteria-laden water is passed through a membrane having a controlled pore size, typically on the order of ~0.20 to ~0.45 µm. These membranes are effective at keeping bacteria from passing through them into a clean water reservoir, but they do not weaken, disable or kill the bacteria. This latter characteristics make such membranes susceptible to bacterial growth, thereby increasing the risks of contamination with biofilms and spore-forming bacteria and reduced flow rates due to clogging.

Silver-loaded ceramic filters use the antimicrobial properties of silver to kill bacteria as they pass through a porous ceramic substrate. To achieve high efficacy, flow rates must be kept low. Further, these filters have a high propensity for clogging. Finally, silver ions are not particularly efficacious in debilitating and killing bacteria in biofilm- and spore forms.

Devices and articles can be provided with coatings that include antimicrobials such as cationic compounds (e.g., quaternary ammonia compounds), silver and copper compounds, and peptides. These coatings are limited in their efficacy against resistant forms of bacteria and have very thin regions of effective antimicrobial effect. These types of coatings are generally designed to prevent surface attachment of bacteria rather than to disinfect.

Certain eluting devices and articles are designed to slowly release anti-bacterial compounds when exposed to moisture. These solids typically been impregnated by antimicrobial agents which, over time, work their way to the surface and are released. The concentrations of solutions eluted from these devices and articles, as well as the efficacy of the employed antimicrobial agents against resistant forms of microbes, are low. The utility of such devices and articles is further reduced in situations where a liquid is to pass through the device due to more rapid depletion of the antimicrobial agent(s).

A solid material capable of preventing bacterial growth, and preferably killing bacteria coming into contact with or close proximity to the solid material, remains desirable. Such a solid preferably can be useful in a variety of forms including, but not limited to, filters, eluting devices, and coatings.

SUMMARY

Liquid compositions effective for disinfection purposes are described in U.S. Pat. Publ. No. 2010/0086576 A1. Those compositions display both moderately high tonicity (i.e., large amounts of osmotically active solutes) and relatively low pH (about $4 \leq pH \leq 6$) which work with surfactants to induce membrane leakage in bacteria, leading to cell lysis. The composition acts at least in part to interrupt or break ionic crosslinks in the macromolecular matrix of a biofilm, facilitating the passage of solutes and surfactant through the matrix to bacteria entrained therein and/or protected thereby. In addition to being lethal toward a wide spectrum of gram positive and gram negative bacteria, these liquid compositions also exhibit lethality toward other microbes such as viruses, fungi, molds, and yeasts.

However, some end-use applications are not conducive to the relatively high concentrations that provide the liquid compositions with their efficacy. These include, but are not limited to, applications where a high concentration of free (unbound) species of these ingredients is unacceptable, applications where an extremely large volume of liquid needs to be disinfected, and applications where such ingredients will be consumed.

The solid materials of the present invention are designed and intended to achieve, in a non-liquid form, a set of characteristics similar to those displayed by the aforementioned liquid compositions: high tonicity and surfactant availability.

These solid materials, adapted to kill bacteria in planktonic, spore and biofilm states, include a crosslinked version of a water soluble polyelectrolyte and entrained surfactant. This combination of components permits the local chemistry within the solid material and in its immediate vicinity, when in use in an aqueous environment, to mimic that of the previously described liquid disinfecting composition: high tonicity and high surfactant concentration. In at least some embodiments, the solid material includes no biocidal additives, particularly active antimicrobial agents.

In certain aspects, the solid material can be prepared by crosslinking a liquid or flowable polyelectrolyte in the presence of the surfactant(s).

Also provided are methods of using the foregoing composition. When a liquid is passed through or in proximity to the solid material, any bacteria or other microorganism is exposed to the local chemistry conditions discussed above: high tonicity, relatively low pH, and available surfactant, a combination that can induce membrane leakage in bacteria leading to cell lysis. These characteristics permit the solid material to be very effective at bypassing and disabling bacterial biofilm and spore defenses, allowing the solid material to kill bacteria in any of its several states.

The solid material can be used to disinfect liquids, in either filter or insert form, and as surface coating that prevents bacterial contamination by killing any bacteria that come into contact therewith. That it can perform these tasks while losing or transmitting very little of its chemical components into the environment being treated is both surprising and advantageous. Further, any chemical components that do enter the environment are relatively benign.

To assist in understanding the following description of various embodiments, certain definitions are provided immediately below. These are intended to apply throughout unless the surrounding text explicitly indicates a contrary intention:

"microbe" means any type of microorganism including, but not limited to, bacteria, viruses, fungi, viroids, prions, and the like;

"antimicrobial agent" means a substance having the ability to cause greater than a 90% (1 log) reduction in the number of one or more of microbes;

"active antimicrobial agent" means an antimicrobial agent that is effective against a microbe only or primarily during the active parts of its lifecycle, e.g., cell division;

"biofilm" means a community of microbes, particularly bacteria and fungi, attached to a surface with the community members being contained in and/or protected by a self-generated macromolecular matrix;

"residence time" means the amount of time that an antimicrobial agent is allowed to contact a bacterial biofilm;

"biocompatible" means presenting no significant, long-term deleterious effects on or in a mammalian species;

"biodegradation" means transformation, via enzymatic, chemical or physical in vivo processes, of a chemical into smaller chemical species;

"polyelectrolyte" means a polymer with multiple mer that include an electrolyte group capable of dissociation in water;

"strong polyelectrolyte" is a polyelectrolyte whose electrolyte groups completely dissociate in water at $3 \leq pH \leq 9$;

"weak polyelectrolyte" is a polyelectrolyte having a dissociation constant of from ~2 to ~10, i.e., partially dissociated at a pH in the range where a strong polyelectrolyte's groups are completely dissociated; and "polyampholyte" is a polyelectrolyte with some mer including cationic electrolyte groups and other mer including anionic electrolyte groups.

Hereinthroughout, pH values are those which can be obtained from any of a variety of potentiometric techniques employing a properly calibrated electrode.

The relevant portions of any specifically referenced patent and/or published patent application are incorporated herein by reference.

DETAILED DESCRIPTION

The antimicrobial solid material can contain as few as two components: a crosslinked polymer network and at least one entrained surfactant, each of which generally is considered to be biocompatible. Certain embodiments of the composition employ no active biocides. In these and other embodiments, the identity of the polymers and surfactants, as well as the concentrations in which each is discharged from the solid material, can be such that recognized toxicity limits are not exceeded during normal use.

The solid material is lethal to planktonic and bacterial cells with high efficacy, is not readily consumed, provides a significant amount of surface area for microbial interactions, and does not create toxicity in solutions being treated. The solid material is not particularly soluble in water under most conditions (e.g., moderate temperatures and solute concentrations), but the polyelectrolyte chains are at least hydrophilic and, where the solid material is to be used in a setting where it might not be immersed in an aqueous medium, preferably hygroscopic, thereby permitting the solid material to swell somewhat when in the presence of moisture, particularly water.

The solid material of the present invention requires some level of water or humidity to function appropriately. This can be determined or defined in a variety of ways. The polyelectrolytes must be capable of localized liquid charge interaction (meaning at least two water molecules are contacting or very near an electrolyte group); alternatively, sufficient water must be present to activate the charge of the electrolyte; and/or sufficient water to permit bacterial growth. As non-limiting examples, gaseous or liquid water can be applied directly to the solid material or can result from other, indirect means, e.g., water vapor contained in breath or ambient air, condensates, etc.

Because the antimicrobial material is solid, it does not itself have a true pH; in use, however, the local pH of any aqueous composition in which it is deployed preferably is lower than ~7 to ensure proper antimicrobial activity. Reduced pH values (e.g., less than ~6.5, ~6.0, ~5.5, ~5.0, ~4.5 and even ~4.0) generally are believed to correlate with increases in efficacy of the solid material, although this effect might not be linear, i.e., the enhancement in efficacy may be asymptotic past a certain hydronium ion concentration. Without wishing to be bound by theory, acidic protons (i.e., hydronium ions) might be involved in breaking ionic crosslinks in the macromolecular matrix of a biofilm.

In addition to more strongly acidic local environments, high local osmolarity conditions also are believed to increase efficacy. Accordingly, larger concentrations of polyelectrolytes, larger concentrations of surfactant, surfactants with shorter chain lengths (e.g., no more than $C_{10}$, typically no more than $C_8$, commonly no more than $C_6$), and surfactants with smaller side groups around the polar group each are more desirable.

The lethality of the surfactant component(s) is increased and/or enhanced when the solid material can provide to the local environment in which it is deployed at least moderate effective solute concentrations (tonicity). (In biological applications, a 0.9% (by wt.) saline solution, which is ~0.3 Osm/L, typically is considered to be have moderate tonicity, while a 3% (by wt.) saline solution, which is ~0.9 Osm/L, generally is considered to be hypertonic.) Without wishing to be bound by theory, higher tonicities may exert higher osmotic pressure to the bacterial cell wall, which increases its susceptibility to interruption by surfactant. Local osmolarity (tonicity) generally increases in proportion to the number and type of electrolytes present in the polymeric network. (By local osmolarity is meant that of a liquid contained in the solid material. While this might vary from place to place throughout the article, preference is given to those solid materials capable of providing high local osmolarities throughout.)

The polyelectrolyte(s) that form the bulk of the solid material preferably are at least somewhat water soluble but also essentially water insoluble after being cross-linked. A partial list of polyelectrolytes having this combination of characteristics included, but are not limited to, strong polyelectrolytes such as polysodium styrene sulfonate and weak polyelectrolytes such as polyacrylic acid, pectin, carrageenan, any of a variety of alginates, polyvinylpyrrolidone, carboxymethylchitosan, and carboxymethylcellulose. Included in potentially useful polyamphyolytes are amino acids and betaine-type cross-linked networks; examples would be hydrogels based on sodium acrylate and trimethylmethacryloyloxyethylammonium iodide, 2-hydroxyethylmethacrylate, or 1-vinyl-3(3-sulfopropyl)imidazolium betaine. Those polymeric materials having electrolyte groups that completely (or nearly completely) dissociate in water and/or provide relatively low local pH values are desired for efficacy are preferred.

Also preferred are those polyelectrolytes having a high density of mer with electrolyte-containing side groups. Without wishing to be bound by theory, the large number of acidic or polar side groups on the polyelectrolyte are believed to function equivalently to the high tonicity solution of the previously described liquid composition.

Several crosslinking mechanisms including but not limited to chemical, high temperature self-crosslinking (i.e., dehydrothermal crosslinking), and irradiation (e.g., e-beam or gamma rays) can be employed. The ordinarily skilled artisan can discern and select an appropriate crosslinking mechanism once a polyelectrolyte is selected.

Another option is to create crosslinks during the polymerization process itself, such as by condensing adjacent sulfonic acid groups to yield sulfonyl crosslinks.

Independent of crosslinking method, the solid material can be formed by crosslinking polymers (or polymerizable monomers) in an aqueous solution contained in a heat conductive mold, followed by rapid freezing and subsequent lyophilizing. The resulting sponge-like material generally takes the shape of the mold in which it was formed. A potential advantage of this process is that it can provide a ready means for removing any hazardous or undesirable precursor chemicals used in the polymerization and/or crosslinking steps. Solids resulting from this type of process often have a spongy appearance, with relatively large pores connected by tortuous paths. Often, pores less than ~0.22 μm, less than ~0.45 μm, less than ~0.80 μm, and less than ~0.85 μm are desirable (based on the diameters of endotoxins, bacteria, and spores); for these and other applications, a solid material with at least some larger pores (e.g., less than ~1, 2, 5, 10, 50, or 100 μm) can be used.

The crosslink density in the solid material plays an important role, specifically, those solid materials with higher crosslink densities tend to maintain higher surfactant concentrations for a longer period of time due to, presumably, longer mean free paths in the polymeric network.

The solid material contains a sufficient amount of surfactant to interrupt or rupture cell walls of bacteria contacting or coming into the vicinity of the solid material. This amount can vary widely based on a variety of factors including, for example, whether a biofilm already exists in the area to be treated (and whether that biofilm is entrenched, a factor which relates to the type of proteins and mass of the macromolecular matrix), the species of bacteria, whether more than one type of bacteria is present, the solubility of the surfactant(s) in the local environment, and the like. The surfactant component(s) generally constitute as low as ~0.03% and as high as ~10%, ~15% or even ~17.5% (all by wt.) of the solid material.

Essentially any material having surface active properties in water can be employed, although those that bear some type of ionic charge are expected to have enhanced antimicrobial efficacy because such charges, when brought into contact with a bacteria, are believed to lead to more effective cell membrane disruption and, ultimately, to cell leakage and lysis. This type of antimicrobial process can kill even sessile bacteria because it does not involve or entail disruption of a cellular process. Cationic surfactants are most desirable followed by, in order, zwitterionic, anionic and non-ionic.

Potentially useful anionic surfactants include, but are not limited to, sodium chenodeoxycholate, N-lauroylsarcosine sodium salt, lithium dodecyl sulfate, 1-octanesulfonic acid sodium salt, sodium cholate hydrate, sodium deoxycholate, sodium dodecyl sulfate, sodium glycodeoxycholate, sodium lauryl sulfate, and the alkyl phosphates set forth in U.S. Pat. No. 6,610,314. Potentially useful cationic surfactants include, but are not limited to, hexadecylpyridinium chloride monohydrate and hexadecyltrimethylammonium bromide, with the latter being a preferred material. Potentially useful nonionic surfactants include, but are not limited to, polyoxyethyleneglycol dodecyl ether, N-decanoyl-N-methylglucamine, digitonin, n-dodecyl B-D-maltoside, octyl B-D-glucopyranoside, octylphenol ethoxylate, polyoxyethylene (8) isooctyl phenyl ether, polyoxyethylene sorbitan monolaurate, and polyoxyethylene (20) sorbitan monooleate. Potentially useful zwitterionic surfactants include, but are not limited to, 3-[(3-cholamidopropyl) dimethylammonio]-2-hydroxy-1-propane sulfonate, 3-[(3-cholamidopropyl) dimethylammonio]-1-propane sulfonate, 3-(decyldimethylammonio) propanesulfonate inner salt, and N-dodecyl-N,N-di-methyl-3-ammonio-1-propanesulfonate. For other potentially useful materials, the interested reader is directed to any of a variety of other sources including, for example, U.S. Pat. Nos. 4,107,328 and 6,953,772 as well as U.S. Pat. Publ. No. 2007/0264310, including quaternary amine compounds of the general formula

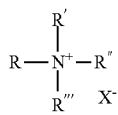

where R, R', R" and R'" are each a $C_1$-$C_{24}$ alkyl, aryl or aralkyl group that can optionally contain one or more P, O, S or N heteroatoms, and X is F, Cl, Br, I or an alkyl sulfate.

The surfactant preferably is present in the polymer network at the time that crosslinking occurs (or the time of polymerization in the case of the type of simultaneous polymerization and condensation discussed above). If it is not, a crosslinked polymer article or film must be post-treated to ensure proper entrainment of the surfactant. A possible method for accomplishing this is immersion of the article or film in an aqueous solution that contains one or more surfactants, followed by removal of excess water via a drying (e.g., thermal or freeze) or evacuation process.

In certain embodiments, the surfactant(s) can be the only antimicrobial agents in the composition, specifically, the composition can be free of active antimicrobial agents.

In addition to the surfactant(s), one or more ionic compounds (salts) can be incorporated into the solid material so as to enhance its ability to create localized regions of high tonicity.

Regardless of how achieved, the local tonicity around the solid material is at least moderately high, with an osmolarity of at least about 0.1 Osm/L being preferred for most applications. Solid materials that create local osmolarities greater than about 0.1 Osm/L will have enhanced bactericidal activity; increases in the osmotic pressure applied to the bacteria enhance antimicrobial efficacy.

A variety of additives and adjuvants can be included to make a solid material more amenable for use in a particular end-use application without negatively affecting its efficacy in a substantial manner. Examples include, but are not limited to, emollients, fungicides, fragrances, pigments, dyes, abrasives, bleaching agents, preservatives (e.g., antioxidants) and the like. Depending on the identity and nature of a particular additive, it can be introduced at any of a variety of times during production of the solid material.

The solid material does not require inclusion of an active antimicrobial agent for efficacy, but such materials can be included in certain embodiments. For example, one or more of bleach, any of a variety of phenols, aldehydes, quaternary ammonium compounds, etc., can be added.

As previously stated, bacteria present in a biofilm derive some inherent protection offered by the EPS/ECPS macromolecular matrix. Without wishing to be bound by theory, the high tonicity and slightly acidic nature of the solid material (as well as the region immediately surrounding it when it is in use) are believed to interfere with and break the ionic crosslinks in the macromolecular matrix of any biofilm passing near or through the material, thus permitting better access to the previously protected bacteria. Additionally, the high tonicity provided in and around the solid material means that an abundance of ions are available, even though some are consumed in the EPS. These ions can assist in killing the bacteria while they remain in the biofilm and after they are freed therefrom, perhaps by making the bacterial cell walls susceptible to being ruptured by the surfactant component(s).

Thus, the solid material that includes one or more surfactants entrained in a polymer network possesses a combination of characteristics and attributes that allow it to be a highly effective yet non-toxic antimicrobial:

1) a capability to provide an aqueous liquid contacting it a local pH (in and/or very near it) of less than 7, preferably less than 6;
2) the polymeric network is hydrophilic (and, where the solid material is intended for use at least some of the time in a non-immersed state, perhaps even hygroscopic);
3) a capability to provide an aqueous liquid contacting it an effective local solution osmolarity (in and/or very near the solid material) of at least ~0.1 Osm/L;
4) a sufficient concentration of one or more surfactants to rupture cell walls of bacteria contacting or coming near to the solid material; and
5) a crosslink density of the polymeric network is great enough to greatly slow the rate of surfactant loss from the material.

This solid material is actively antimicrobial, has greater antimicrobial efficacy against bacteria in resistant forms, is not rapidly consumed, and does not create toxicity in the medium being treated.

The solid material can take any of a variety of intermediate and final shapes or forms including, but are not limited to, a spongy solid that is permeable to vapor and or liquids; a molded, extruded or deposited sheet; and an extruded fiber or thread. Once in a particular shape, the material then can be further processed or manipulated so as to provide a desired shape, e.g., a sheet good can be rolled or folded so as to provide a membrane of a particular geometry. Thus whether the material is used in its manufactured form or it is post processed by thermal forming, mechanical shaping, lamination, granulation, pulverization, etc., it is considered to be within the present disclosure.

A single, non-limiting example of a potential use for a solid antimicrobial material is as a filter (or part of a filtration device) to be placed in the flow path of a vapor or liquid passing there-through, -over or -by. Such a material can be housed, sealed, or adhered in a variety of ways so as to permit fluid flow to be directed through, around, or over it.

A filter can be provided by making a spongy solid (via, for example, a lyophilization process such as the one described above) with a surfactant trapped therein. Water can be passed through or past the spongy solid, which will work as a filter device, which is actively antimicrobial and kills any bacteria passing through the element.

Such a filter can have high flow rates because of its active antimicrobial nature and, therefore, can have larger pore sizes than current sterile filters which rely on extremely small pores to prevent passage of bacteria through the filter. Larger pores also mean that such a filter will be less susceptible to clogging, thus increasing its viable lifecycle. Thus, the resulting filtration device has high bactericidal activity toward planktonic and bacterial cells, permits high fluid flow rates, is less susceptible to clogging, and produces disinfected water which is non-toxic when ingested.

As an alternative to a spongy, amorphous mass, a much more structured form, e.g., a fabric (woven or nonwoven) made from or incorporating threads provided from a solid antimicrobial material of the present invention, also can be employed for such filtration applications.

In addition to water filtration, other potential uses for solid materials of the present invention include, but are not limited to, air filters, odor controlling articles (e.g., clothing such as socks, shoe inserts, etc.), pool water treatment articles, disinfecting wipes, mine waste pool barriers (to prevent acidic leakage due to bacterial activity), bandages, humidifier wicking elements, layers in personal protection articles such as diapers and feminine hygiene products, and the like.

The solid material of the present invention also can be used as an antimicrobial surface coating or external surface layer for the prevention of bacterial contamination of the protected surface. In this manner, the material will kill bacteria, in any form, coming into contact with the surface of the material. Potential end use applications for such coatings include, but are not limited to, cooler surfaces, refrigerator interiors, drip pans (e.g., refrigerators, dehumidifiers, etc.), food storage containers, tracheotomy tubes, external surfaces of temporarily or permanently implanted medical devices, contact surfaces in medical equipment (e.g., fluid lines, fittings, joints, reservoirs, covers, etc.), reagent bottles, telephone and remote control surfaces (e.g., buttons), medical devices intended to contact more than one patient (e.g., blood pressure cuffs, stethoscopes, wheelchairs, gurneys, etc.), plumbing fixtures, pipes and traps, recreational vehicle cisterns and tanks, shower walls and components, canteens, beverage dispensers and transfer lines, baby feeding equipment (e.g., bottles, nipples, etc.), pacifiers, teething rings, toys, playground and exercise equipment, outdoor equipment (e.g., tents, boat covers, sleeping bags, etc.), and the like.

As is clear from the foregoing description, the solid material may take many different physical forms and find use in a variety of devices. Its components can be provided from a wide variety of materials, and its polymer network can be crosslinked in a variety of ways. Thus, the ordinarily skilled artisan understands that the functionality of the components and not their specific identity or manner of processing is that which is most important; the ever evolving fields of chemistry and polymer science are anticipated to provide additional options not known at the time of this writing that provide similar functionality. (By way of non-limiting example, surfactants are described here as a key component for providing bactericidal activity; however, newly developed compounds that do not fit entirely within the definition of "surfactant" yet still possess the types of charged or polar side groups that provide the same functional mechanism are quite reasonably expected to be useful in solid material.)

While various embodiments of the present invention have been provided, they are presented by way of example and not limitation. The following claims and their equivalents define the breadth and scope of the inventive methods and compositions, and the same are not to be limited by or to any of the foregoing exemplary embodiments.

That which is claimed is:

1. An article having at least one surface adapted to kill bacteria coming in contact therewith, said article comprising a substrate and, disposed on at least one surface of said substrate, a solid antimicrobial coating that consists of (a) a hydrophilic network of chemically crosslinked polyacrylic acid and (b) one or more cationic surfactants entrained in said polymer network, said coating being adapted to be effective when in contact with water.

2. The article of claim 1 wherein said substrate is a medical device intended for temporary implantation and wherein said surface is an external surface of said device.

3. The article of claim 1 wherein said one or more cationic surfactants constitute from 0.03 to 10 weight percent of said solid antimicrobial coating.

4. The article of claim 3 wherein said one or more cationic surfactants comprises a quaternary ammonium halide.

5. The article of claim 4 wherein said one or more cationic surfactants is a quaternary ammonium halide.

6. The article of claim 1 wherein said one or more cationic surfactants comprises a quaternary ammonium halide.

7. The article of claim 6 wherein said one or more cationic surfactants is a quaternary amine compound.

8. The article of claim 1 wherein said substrate is a tracheotomy tube.

9. The article of claim 1 wherein said substrate is a contact surface of medical equipment.

10. The article of claim 1 wherein said substrate is a patient contact surface of a medical device selected from blood pressure cuffs, stethoscopes, wheelchairs and gurneys.

* * * * *